United States Patent
Kurihara et al.

(10) Patent No.: US 11,932,679 B2
(45) Date of Patent: Mar. 19, 2024

(54) AGENT FOR RESTORING VISUAL FUNCTION OR AGENT FOR PREVENTING DETERIORATION IN VISUAL FUNCTION

(71) Applicants: KEIO UNIVERSITY, Tokyo (JP); NAGOYA INSTITUTE OF TECHNOLOGY, Nagoya (JP)

(72) Inventors: Toshihide Kurihara, Tokyo (JP); Yusaku Katada, Tokyo (JP); Hiromitsu Kunimi, Tokyo (JP); Kazuo Tsubota, Tokyo (JP); Hideki Kandori, Nagoya (JP)

(73) Assignees: Keio University, Tokyo (JP); Nagoya Institute of Technology, Nagoya (JP)

(*) Notice: Subject to any disclaimer, the term of this patent is extended or adjusted under 35 U.S.C. 154(b) by 875 days.

(21) Appl. No.: 16/329,631

(22) PCT Filed: Sep. 1, 2017

(86) PCT No.: PCT/JP2017/031579
§ 371 (c)(1),
(2) Date: Feb. 28, 2019

(87) PCT Pub. No.: WO2018/043707
PCT Pub. Date: Mar. 8, 2018

(65) Prior Publication Data
US 2019/0194294 A1 Jun. 27, 2019

(30) Foreign Application Priority Data
Sep. 2, 2016 (JP) ................... 2016-172149

(51) Int. Cl.
*C07K 14/72* (2006.01)
*A61K 31/7088* (2006.01)
*A61K 35/76* (2015.01)
*A61K 38/00* (2006.01)
*A61K 48/00* (2006.01)
*A61P 27/02* (2006.01)
*C07K 14/195* (2006.01)
*C07K 14/705* (2006.01)
*C07K 19/00* (2006.01)
*C12N 15/09* (2006.01)
*C12N 15/86* (2006.01)

(52) U.S. Cl.
CPC ........ *C07K 14/723* (2013.01); *A61K 31/7088* (2013.01); *A61K 35/76* (2013.01); *A61K 38/00* (2013.01); *A61K 48/00* (2013.01); *A61P 27/02* (2018.01); *C07K 14/195* (2013.01); *C12N 15/09* (2013.01); *C12N 15/86* (2013.01); *C07K 14/705* (2013.01); *C07K 19/00* (2013.01); *C12N 2750/14143* (2013.01)

(58) Field of Classification Search
CPC .. C07K 14/723; C07K 14/195; C07K 14/705; C07K 19/00; C07K 2319/00; A61K 31/7088; A61K 35/76; A61K 38/00; A61K 48/00; A61P 27/02; C12N 15/09; C12N 15/86; C12N 2750/14143; C12N 2740/16043; C12N 2750/14171
See application file for complete search history.

(56) References Cited

U.S. PATENT DOCUMENTS

| | | | |
|---|---|---|---|
| 7,196,175 B2 | 3/2007 | Tamatani et al. | |
| 2016/0038409 A1* | 2/2016 | Pan | A61K 31/7088 424/134.1 |
| 2019/0194294 A1 | 6/2019 | Kurihara | |
| 2022/0025018 A1* | 1/2022 | Kurihara | C07K 14/723 |
| 2022/0273761 A1 | 9/2022 | Kurihara et al. | |

FOREIGN PATENT DOCUMENTS

| | | |
|---|---|---|
| EP | 2547762 B1 | 4/2018 |
| EP | 3508212 A1 | 7/2019 |
| JP | 11-29599 A | 2/1999 |

(Continued)

OTHER PUBLICATIONS

Yusaku Katada et al., "Study on effect of reconstructing vision using chimeric rhodopsin, Journal of the Japanese Ophthalmological Society," 122:259 (Mar. 9, 2018) (English Translation attached).
Yusaku Katada et al., "Study on effect of reconstructing vision using chimeric rhodopsin," The 122nd Annual Meeting of the Japanese Ophthalmological Society, abstract, https://www.micenavi.jp/122jos/search/detail_session/id:125 (2018) (English Translation attached).

(Continued)

*Primary Examiner* — Janet L Epps-Smith
*Assistant Examiner* — Alexander W Nicol
(74) *Attorney, Agent, or Firm* — HALEY GUILIANO LLP; James F. Haley, Jr.

(57) ABSTRACT

The purpose of the present invention is to provide an agent for restoring a visual function or an agent for preventing the deterioration in a visual function, which has an excellent visual function restoring ability. The agent for regenerating a visual function or the agent for preventing the deterioration in a visual function according to the present invention contains, as an active ingredient, a chimeric protein having both an amino acid sequence for a microorganism-origin ion-transporting receptor rhodopsin and an amino acid sequence for an animal-origin G-protein-coupled receptor rhodopsin. The chimeric protein is preferably one in which an amino acid sequence for a cytoplasm-side second loop and/or a cytoplasm-side third loop in the amino acid sequence for the microorganism-origin ion-transporting receptor rhodopsin is substituted by an amino acid sequence for a cytoplasm-side second loop and/or a cytoplasm-side third loop in the G-protein-coupled receptor rhodopsin.

5 Claims, 3 Drawing Sheets
Specification includes a Sequence Listing.

(56) References Cited

FOREIGN PATENT DOCUMENTS

| | | | |
|---|---|---|---|
| JP | 2009536219 | 10/2009 | |
| JP | 2014500716 | 1/2014 | |
| JP | 2016519063 | 6/2016 | |
| KR | 101061482 B1 | 9/2011 | |
| WO | WO2007131180 | 11/2007 | |
| WO | WO2011/030964 | * 3/2011 | ............... C12N 9/96 |
| WO | WO2011030964 | 3/2011 | |
| WO | 2012/061679 A2 | 5/2012 | |
| WO | WO2014160281 | 10/2014 | |
| WO | WO2015138616 | 9/2015 | |
| WO | WO2020148913 | 7/2020 | |
| WO | WO2021049634 | 3/2022 | |

OTHER PUBLICATIONS

Yusaku Katada et al., "Study on effect of reconstructing vision using chimeric rhodopsin," The 122nd Annual Meeting of the Japanese Ophthalmological Society, Poster Apr. 2018 (English Translation attached).

Yusaku Katada et al., "Study on effect of reconstructing vision using chimeric rhodopsin," The 122nd Annual Meeting of the Japanese Ophthalmological Society, short title list, Apr. 2018 https://convention.jtbcom.co.jp/122jos/program/index.html (English Translation attached).

Kurihara, "From algae to humans: Challenge to transcendental retinal treatment," The 72nd Annual Congress of Japan Clinical Ophthalmology at Tokyo International Forum (Oct. 12, 2018) (no English Translation).

Toshihide Kurihara, Institute for Protein Research, Osaka University Seminar: Frontiers of Sensory research in Retina Jan. 20, 2018 (no English Translation).

Kurihara, "Visual restoration utilizing optogenetics for retinal degeneration," Journal of Japanese Ophthalmological Society, 123:55 (2019) (5 pages) (English Translation attached).

Zhao et al., "Improved expression of halorhodopsin for light-induced silencing of neuronal activity," Brain Cell Biology, 36:141-154 (2008) (English Translation attached).

Sasaki et al., "Chimeric proton-pumping rhodopsins containing the cytoplasmic loop of bovine rhodopsin", PLOS One, 9(3):1-12, e91323 (2014).

Bi et al., "Ectopic Expression of a Microbial-Type Rhodopsin Restores Visual Responses in Mice with Photoreceptor Degeneration," Neuron, 50(1):23-33 (2006).

Tomita et al., "Restoration of the majority of the visual spectrum by using modified Volvox channelrhodopsin-1," American Society of Gene & Cell Therapy, 22(8):1434-1440 (2014).

"Gyoseki Shokai: Dobutsu-gata Rhodopsin to Biseibutsu-gata Rhodopsin no Chimeric Proteins no Kino", Grant-in-Aid for Scientific Research on Innovative Areas 'Yawarakana Bunshikei' News Letter Heisei 26 Nen The April issue, Apr. 2014, No. 8, p. 34, <URL, http://www.yawaraka.org/letter/NL08_1404.pdf> (JP language with English translation).

Granovsky, et al., "Objective correlate of subjective pain perception by contact heat-evoked potentials," The Journal of Pain, 9(1):53-63 (2008).

Huang, et al., "A novel approach to predict subjective pain perception from single-trial laser-evoked potentials," Neuroimage, 81:283-293 (2013).

Altschul et al., "Basic Logal Alignment Search Tool", J. Mol. Biol. 215: 403-410 (1990).

Batzer et al., "Enhanced evolutionary PCR using oligonucleotides with inosine at the 3'-terminus", Nucleic Acid Res. 19: 5081 (1991).

Chow et al., "High-performance genetically targetable optical neural silencing by light-driven proton pumps", Nature 463: 98-102 (2010).

Dalbadie-McFarland et al., "Oligonucleotide-directed nutagenesis as a general and powerful method for studies of protein function", Proc. Natl. Acad. Sci. USA 79: 6409-6413 (1982).

Karlin et al., "Applications and statistics for multiple high-scoring segments in molecular sequences", Proc. Natl. Acad. Sci. USA 90: 5873-5877 (1993).

Li et al., "Fast noninvasive activation and inhibition of neural and network activity by vertebrate rhodopsin and green algae channelrhodopsin", PNAS 102(49): 17816-17821 (2005).

Mark et al., "Site-specific mutagenesis of the human fibroblast interferon gene", Proc. Natl. Acad. Sci. USA 81: 5662-5666 (1984).

Ohtsuka et al., "An Alternative Approach to Deoxyoligonueleotides as Hybridization Probes by Insertion of Deoxyinosine at Ambiguous Codon Positions*", J. Biol. Chem. 260(5): 2605-2608 (1985).

Rossolini et al., "Use of deoxyinosine-containing primers vs degenerate primers for polymerase chain reaction based on ambiguous sequence information", Mol. Cell. Probes 8: 91-98 (1994).

Stockklausner et al., "A sequence motif responsible for ER export and surface expression of Kir2.0 inward rectifier K+ channels", FEBS Letters 493: 129-133 (2001).

Wang, A. et al., "Site-Specific Mutagenesis of the Human Interleukin-2 Gene: Structure-Function Analysis of the Cysteine Residues", Science 224(4656), 1431-1433 (1984).

Zoller et al., "Oligonucleotide-directed mutagenesis using M13-derived vectors: an efficient and general procedure for the production of point mutations in any fragment of DNA", Nucleic Acids Research 10(20): 6487-6500 (1982).

Morgan, "Plasmids 101: The Promoter Region—Let's Go!," Apr. 3, 2014 (8 total pages) (https://blog.addgene.org/plasmids-101-the-promoter-region).

SignaGen Laboratories, A Gene Delivery Company, "Common promoters for eukaryotes and prokaryotes" Oct. 16, 2015 (4 total pages) (https:// signagen.com/blog/2015/10/16/common-promoters-for-eukaryotes-and-prokaryotes/).

U.S. Appl. No. 17/424,144, filed Jul. 19, 2021, Toshihide Kurihara.
U.S. Appl. No. 17/642,923, filed Mar. 14, 2022, Toshihide Kurihara.
U.S. Appl. No. 17/731,976, filed Apr. 28, 2022, Toshihide Kurihara.

* cited by examiner (b)

(a)

AGENT FOR RESTORING VISUAL FUNCTION OR AGENT FOR PREVENTING DETERIORATION IN VISUAL FUNCTION

CROSS-REFERENCE TO RELATED APPLICATIONS

This application is a United States National Phase Application filed under 35 U.S.C. § 371 from International Patent Application No. PCT/JP2017/031579, filed on Sep. 1, 2017, which claims priority from Japanese Patent Application No. 2016-172149, filed on Sep. 2, 2016. The contents and disclosures of each of these applications are incorporated by reference herein in their entireties.

SEQUENCE LISTING

The instant application contains a Sequence Listing which has been submitted electronically as a text file in ASCII format and is hereby incorporated by reference in its entirety. Said text file, created on Feb. 28, 2019, is named 000175-0001-301.SL.txt and is 18,442 bytes in size.

TECHNICAL FIELD

The present invention relates to an agent for restoring visual function or agent for preventing deterioration in visual function.

BACKGROUND ART

Rhodopsin is a photosensitive receptor with a seven transmembrane structure in the retina of humans and animals. Ion channel and ion pump type rhodopsins derived from microorganisms are also known.

For example, Non Patent Literature 1 discloses an ion channel type rhodopsin, channelrhodopsin 2 (ChR2). Further, Non Patent Literature 2 has reported that a certain visual function is restored in mice/rats by introducing a mutant channelrhodopsin into retinal ganglion cells.

CITATION LIST

Non Patent Literature

[NPL 1] Bi et al., "Ectopic expression of a microbial-type rhodopsin restores visual responses in mice with photoreceptor degeneration." Neuron. 2006; 50(1): 23-33
[NPL 2] Tomita et al., "Restoration of the Majority of the Visual Spectrum by Using Modified Volvox Channelrhodopsin-1", Molecular Therapy (2014); 22 8, 1434-1440

SUMMARY OF INVENTION

Technical Problem

However, the effect of restoring visual function of ion channel type rhodopsins is still not considered sufficient, such that there is room for improvement.

The present invention has been conceived in view of the above circumstances. The objective of the invention is to provide an agent for restoring visual function or agent for preventing deterioration in visual function with an excellent capability to restore visual function.

Solution to Problem

The inventors have found that a chimeric protein prepared by fusing two completely different rhodopsins, i.e., a microorganism derived ion transport rhodopsin and an animal derived G protein-coupled receptor rhodopsin in fact has an excellent capability to restore visual function to complete the present invention. More specifically, the present inventions are composed of the following configurations.

(1) An agent for restoring visual function or agent for preventing deterioration in visual function comprising, as an active ingredient, a chimeric protein having an amino acid sequence of a microorganism derived ion transport receptor rhodopsin and an amino acid sequence of an animal derived G protein-coupled receptor rhodopsin.

(2) The agent for restoring visual function or agent for preventing deterioration in visual function of (1), wherein the chimeric protein has an amino acid sequence of a second loop on a cytoplasm side and/or a third loop on a cytoplasm side of the amino acid sequence of the microorganism derived ion transport receptor rhodopsin, replaced with an amino acid sequence of a second loop on a cytoplasm side and/or a third loop on a cytoplasm side of the G protein-coupled receptor rhodopsin.

(3) The agent for restoring visual function or agent for preventing deterioration in visual function of (1) or (2), wherein the microorganism derived ion transport receptor rhodopsin is a rhodopsin derived from a microorganism of the *Gloeobacter* genus, and the G protein-coupled receptor rhodopsin is a bovine or human derived rhodopsin.

(4) The agent for restoring visual function or agent for preventing deterioration in visual function of any one of (1) to (3), wherein the chimeric protein has an amino acid sequence encoded by a DNA of any one of the following (a) to (d):

(a) a DNA having a base sequence encoding the amino acid sequence of any one of SEQ ID NOs: 1 to 4;
(b) a DNA having a base sequence that can hybridize under a stringent condition with a base sequence complementary to a base sequence encoding the amino acid sequence of any one of SEQ ID NOs: 1 to 4;
(c) a DNA having a base sequence encoding the amino acid sequence of any one of SEQ ID NOs: 1 to 4 with one or more amino acid substitutions, deletions, and/or additions, and having a visual function restoring capability or visual function deterioration preventing capability; and
(d) a DNA consisting of a base sequence encoding an amino acid sequence having 90% or greater homology with the amino acid sequence of any one of SEQ ID NOs: 1 to 4 and having a visual function restoring capability or visual function deterioration preventing capability.

(5) An agent for restoring visual function or agent for preventing deterioration in visual function comprising, as an active ingredient, an expression vector into which a DNA encoding the amino acid sequence of the chimeric protein of any one of (1) to (4) is incorporated.

(6) The agent for restoring visual function or agent for preventing deterioration in visual function of any one of (1) to (5) for use in treating or preventing retinitis pigmentosa.

(7) An adeno-associated virus (AAV) vector or lentivirus vector, to which a sequence of a chimeric protein having an amino acid sequence of a microorganism derived ion transport receptor rhodopsin and an amino acid sequence of an animal derived G protein-coupled receptor rhodopsin is inserted.

(8) Use of an adeno-associated virus (AAV) vector or lentivirus vector, to which a sequence of a chimeric protein having an amino acid sequence of a microorganism derived ion transport receptor rhodopsin and an amino acid sequence of an animal derived G protein-coupled receptor rhodopsin is inserted, for the manufacture of a medicament for restoring visual function or preventing deterioration in visual function.

Advantageous Effects of Invention

The present invention can attain an excellent capability to restore visual function.

DESCRIPTION OF EMBODIMENTS

Figure 1:
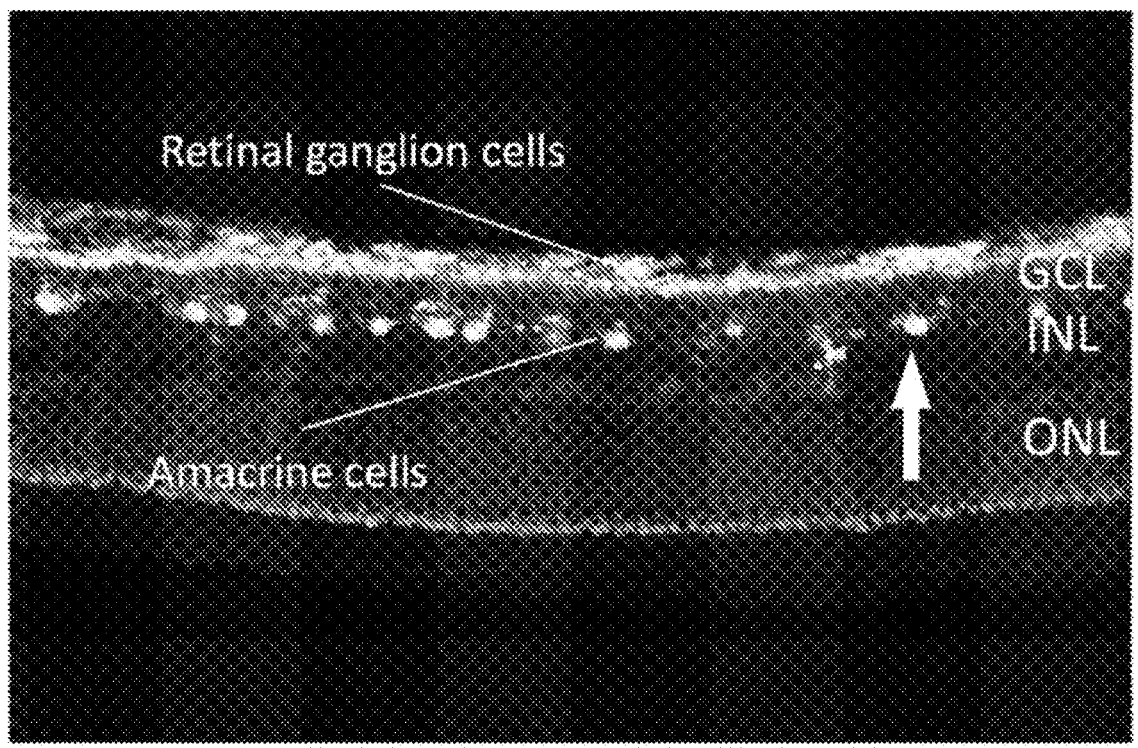
FIG. 1 is an image of a retina of a wild-type mouse injected with AAV2-CAGGS-EGFP-WPRE-pA into the vitreous body observed under a fluorescence microscope.

While the specific embodiments of the invention are described in detailed hereinafter, the present invention is not limited in any manner to the following embodiments. The present invention can be practiced by applying an appropriate modification within the scope of the objects of the invention. Explanation is omitted when appropriate for portions where a description would be redundant, but such an omission does not limit the gist of the invention.

<Agent for Restoring Visual Function or Agent for Preventing Deterioration in Visual Function>

The agent for restoring visual function or agent for preventing deterioration in visual function of the invention comprises, as an active ingredient, a chimeric protein having an amino acid sequence of a microorganism derived ion transport receptor rhodopsin and an amino acid sequence of an animal derived G protein-coupled receptor rhodopsin.

Rhodopsin has a pigment called retinal inside, which is activated by receiving light to transmit a visual signal to the brain. Microorganism derived ion transport receptor rhodopsins can be repeatedly activated by absorbing light because they do not release retinal by light irradiation, but are unable to activate a G protein as in animal derived G protein-coupled receptor rhodopsins. Meanwhile, according to the present invention, high activity through the endogenous G protein due to the G protein-coupled receptor rhodopsin while retaining the function of repeated activation of the microorganism derived ion transport receptor/ion channel type receptor rhodopsin can be attained by fusing an animal derived G protein-coupled receptor rhodopsin to a microorganism derived ion transport receptor rhodopsin that can be repeatedly used. Such a fusion rhodopsin is expected to attain an excellent visual restoring effect. In this manner, microorganism derived rhodopsins and animal derived G protein-coupled receptors are receptors with completely different functions. The inventors have actually found that a chimeric protein combining two such receptors has an excellent capability to restore a visual function. Since such a chimeric protein can be repeatedly activated while having high activity as discussed above, an effect of preventing the deterioration in visual function (e.g., suppressing the progression of retinal diseases such as retinitis pigmentosa) is also expected.

Examples of ion transport receptor rhodopsins include ion pump type receptor rhodopsins and ion channel type receptor rhodopsins.

The chimeric protein of the invention is a chimeric protein of a microorganism derived ion transport receptor rhodopsin and a G protein-coupled receptor rhodopsin, having a seven transmembrane structure. It is preferable in the present invention that a chimeric protein of a microorganism derived ion transport receptor rhodopsin and a G protein-coupled receptor rhodopsin is designed to have both high level of function for repeatedly activating the microorganism derived ion transport receptor rhodopsin and G protein activity due to the G protein-coupled receptor rhodopsin. From this viewpoint, it is preferable that the chimeric protein of the invention has an amino acid sequence of a second loop on a cytoplasm side and/or a third loop on a cytoplasm side of the amino acid sequence of the microorganism derived ion transport receptor rhodopsin substituted with an amino acid sequence of a second loop on a cytoplasm side and/or a third loop on a cytoplasm side of the G protein-coupled receptor rhodopsin, because both activities are maintained high and especially because high visual function restoring capability is attained. The "second loop on a cytoplasm side" and "third loop on a cytoplasm side" refer to loops at position 2 from the N-terminus side and position 3 from the N-terminus side among the seven loops, respectively.

Examples of microorganism derived ion transport receptor rhodopsins include rhodopsins derived from microorganisms, e.g., belonging to eubacteria such as the *Gloeobacter* genus and the like, eukaryotes such as the Volvox genus, *Chlamydomonas* genus, *Guillardia* genus, and the like. Examples of the *Gloeobacter* genus include *Gloeobacter violaceus* and the like. Examples of the *Volvox* genus include *Volvox carteri* and the like. Examples of the *Chlamydomonas* genus include *Chlamydomonas reinhardtii* and the like. Examples of *Guillardia* genus include *Guillardia* theta and the like. Conformational compatibility with a G protein activation loop and the membrane translocation efficiency are considered important for attaining a higher visual restoration/prophylactic effect. Microorganism derived ion transport receptor rhodopsins are thus preferably of the *Gloeobacter* genus due to the especially excellent conformational compatibility with a G protein activation loop and membrane translocation efficiency. *Gloeobacter violaceus* is especially preferable among microorganisms of the *Gloeobacter* genus. It is also preferable to combine and fuse those of a microorganism of the *Gloeobacter* genus with a bovine or human derived G protein-coupled receptor rhodopsin among animal derived G protein-coupled receptor rhodopsins. The *Gloeobacter* genus is also preferable in terms of having an important property of being expressed well in *E. coli*, which is a *eubacterium*, and human cells, which are eukaryotes.

Examples of animal derived G protein-coupled receptor rhodopsins include rhodopsins derived from a cow, human, mouse, rat, cat, dog, swine, sheep, horse, or the like. Among them, bovine and human derived rhodopsins are particularly preferable.

More specifically, a chimeric protein preferably has an amino acid sequence encoded by the DNA of any one of the following (a) to (d):

(a) a DNA having a base sequence encoding the amino acid sequence of any one of SEQ ID NOs: 1 to 4;
(b) a DNA having a base sequence that can hybridize under a stringent condition with a base sequence complementary to a base sequence encoding the amino acid sequence of any one of SEQ ID NOs: 1 to 4;
(c) a DNA having a base sequence encoding the amino acid sequence of any one of SEQ ID NOs: 1 to 4 with one or more amino acid substitutions, deletions, and/or additions, and having a visual function restoring capability or visual function deterioration preventing capability; and
(d) a DNA consisting of a base sequence encoding an amino acid sequence having 90% or greater homology with the amino acid sequence of any one of SEQ ID NOs: 1 to 4 and having a visual function restoring capability or visual function deterioration preventing capability.

The second loop on the cytoplasm side of the G protein-coupled receptor rhodopsin discussed above preferably has an amino acid encoding encoded by the DNA of the following (e) to (h):

(e) a DNA having a base sequence encoding the amino acid sequence of SEQ ID NO: 5 or 6;
(f) a DNA having a base sequence that can hybridize under a stringent condition with a base sequence complementary to a base sequence encoding the amino acid sequence of SEQ ID NO: 5 or 6;
(g) a DNA having a base sequence encoding the amino acid sequence of SEQ ID NO: 5 or 6 with one or more amino acid substitutions, deletions, and/or additions; and
(h) a DNA consisting of a base sequence encoding an amino acid sequence having 90% or greater homology with the amino acid sequence of SEQ ID NO: 5 or 6.

The third loop on the cytoplasm side of the G protein-coupled receptor rhodopsin discussed above preferably has an amino acid encoding encoded by the DNA of the following (i) to (1):

(i) a DNA having a base sequence encoding the amino acid sequence of SEQ ID NO: 7;
(j) a DNA having a base sequence that can hybridize under a stringent condition with a base sequence complementary to a base sequence encoding the amino acid sequence of SEQ ID NO: 7;
(k) a DNA having a base sequence encoding the amino acid sequence of SEQ ID NO: 7 with one or more amino acid substitutions, deletions, and/or additions; and
(l) a DNA consisting of a base sequence encoding an amino acid sequence having 90% or greater homology with the amino acid sequence of SEQ ID NO: 7.

A base sequence encoding the amino acid sequence of any one of SEQ ID NOs: 1 to 4 is a preferred sequence of a base sequence encoding the chimeric protein of the invention. The base sequence encoding the amino acid sequence of any one of SEQ ID NOs: 1 to 4 has a visual function restoring capability or visual function deterioration preventing capability. As used herein, "base sequence has a visual function restoring capability or visual function deterioration preventing capability means that a polypeptide encoded by the base sequence has a visual function restoring capability or visual function deterioration preventing capability. A DNA having a base sequence encoding the amino acid sequence of any one of SEQ ID NOs: 1 to 4 further encompasses various mutants and homologs having a visual function restoring capability or visual function deterioration preventing capability. Mutants and homologs of a DNA having a base sequence encoding the amino acid sequence of any one of SEQ ID NOs: 1 to 4 encompass, for example, DNAs having a base sequence that can hybridize under a stringent condition with a base sequence encoding the amino acid sequence of any one of SEQ ID NOs: 1 to 4. Further, mutants and homologs of a DNA having a base sequence encoding the amino acid sequence of any one of SEQ ID NOs: 5 to 7 encompass DNAs having a base sequence that can hybridize under a stringent condition with a base sequence encoding the amino acid sequence of any one of SEQ ID NOs: 5 to 7. Examples of "stringent condition" include conditions for performing a reaction at 40 to 70° C. (preferably 50 to 67° C. and more preferably 60 to 65° C.) in a normal hybridization buffer and washing in a detergent with a salt concentration of 15 to 300 mM (preferably 15 to 150 mM, more preferably 15 to 60 mM, and still more preferably 30 to 50 mM).

Any one of SEQ ID NOs: 1 to 4 can be used as the amino acid sequence of the chimeric protein of the invention. A DNA encoding the amino acid sequence of the chimeric protein of the invention encompasses DNAs having a base sequence encoding the amino acid sequence of any one of SEQ ID NOs: 1 to 4 with one or more amino acid substitutions, deletions, and/or additions. In this regard, "one or more" in any one of SEQ ID NOs: 1 to 4 is generally 50 amino acids or less, preferably 30 amino acids or less, and still more preferably 10 amino acids or less (e.g., 5 amino acids or less, 3 amino acids or less, or one amino acid). Further, "one or more" in any one of SEQ ID NOs: 5 to 7 is generally 6 amino acids or less, preferably 5 amino acids or less, and still more preferably 4 amino acids or less (e.g., 3 amino acids or less, 2 amino acids or less, and one amino acid). When maintaining a visual function restoring capability or visual function deterioration preventing capability of a chimeric protein, it is desirable that an amino acid residue to be mutated is mutated to another amino acid which conserves the property of an amino acid side chain. Examples of properties of an amino acid side chain include hydrophobic amino acids (A, I, L, M, F, P, W, Y, V), hydrophilic amino acids (R, D, N, C, E, Q, G, H, K, S, T), amino acids with an aliphatic side chain (G, A, V, L, I, P), amino acids with a hydroxyl group containing side chain (S, T, Y), amino acids with a sulfur atom containing side chain (C, M), amino acids with a carboxylic acid and amide containing side chain (D, N, E, Q), amino acids with a base containing side chain (R, K, H), and amino acids with an aromatic containing side chain (H, F, Y, W) (each symbol within the parenthesis represents the one-letter code of an amino acid). It is known that proteins having an amino acid sequence modified by one or more amino acid residue deletions, additions, and/or substitutions with another amino acid to the amino acid sequence maintain the biological activity thereof (Mark, D. F. et al., Proc. Natl. Acad. Sci. USA (1984) 81, 5662-5666, Zoller, M. J. & Smith, M. Nucleic Acids Research (1982) 10, 6487-6500, Wang, A. et al., Science 224, 1431-1433, Dalbadie-McFarland, G. et al., Proc. Natl. Acad. Sci. USA (1982) 79, 6409-6413).

Mutants and homologs of a DNA having a base sequence encoding the amino acid sequence of any one of SEQ ID NOs: 1 to 4 encompass DNAs consisting of a base sequence having high homology with a base sequence encoding the amino acid sequence of any one of SEQ ID NOs: 1 to 4. Such a DNA preferably has homology of 90% or greater, and still more preferably 95% or greater (96% or greater, 97% or greater, 98% or greater, or 99% or greater) with a base sequence encoding the amino acid sequence of any one of SEQ ID NOs: 1 to 4. Mutants and homologs of a DNA having a base sequence encoding the amino acid sequence of any one of SEQ ID NOs: 5 to 7 encompass DNAs consisting of a base sequence having high homology with a base sequence encoding the amino acid sequence of any one of SEQ ID NOs: 5 to 7. Such a DNA preferably has homology of 90% or greater, and still more preferably 95% or greater (96% or greater, 97% or greater, 98% or greater, or 99% or greater) with a base sequence encoding the amino acid sequence of any one of SEQ ID NOs: 5 to 7. The homology of amino acid sequences and base sequences can be determined by the algorithm BLAST developed by Karlin and Altschul (Proc. Natl. Acad. Sci. USA 90: 5873-5877, 1993). Programs called BLASTN and BLASTX have been developed based on this algorithm (Altschul et al. J. Mol. Biol. 215: 403-410, 1990). When analyzing a base sequence using BLASTN based on BLAST, parameters are set to, for example, score=100 and wordlength=12. When analyzing an amino acid sequence using BLASTX based on BLAST, parameters are set to, for example, score=50 and wordlength=3. When using BLAST and Gapped BLAST programs, the default parameters of each program are used. The specific approaches of these analysis methods are known (http://www.ncbi.nlm.nih.gov).

As used herein, "DNA" may be a sense strand or an antisense strand (e.g., can be used as a probe). The shape thereof may be a single strand or double strand. DNA may also be genomic DNA, cDNA, or synthesized DNA.

The method of obtaining DNA of the invention is not particularly limited. Examples thereof include known methods such as a method of obtaining cDNA by reverse transcription from mRNA (e.g., RT-PCR method), method of adjusting from genomic DNA, method of synthesizing by chemical synthesis, and method of isolating from a genomic DNA library or a cDNA library (see, for example, Japanese Laid-Open Publication No. 11-29599).

A chimeric protein used in the agent for restoring visual function or agent for preventing deterioration in visual function of the invention can be prepared, for example, by using a transformant introduced with an expression vector comprising a DNA encoding the aforementioned chimeric protein. For example, the transformant is first cultured under suitable conditions to synthesize a chimeric protein encoded by the DNA. The synthesized protein can then be retrieved from the transformant or culture to obtain the chimeric protein of the invention.

More specifically, this can be made by inserting a DNA encoding the aforementioned chimeric protein into a suitable expression vector. The "suitable vector" may be any vector that can be replicated and retained or self-proliferate within various hosts of prokaryotes and/or eukaryotes. The vector can be appropriately selected depending on the objects of use. For obtaining a large quantity of DNA, a high copy number vector, for example, can be selected. For obtaining a polypeptide (chimeric protein), an expression vector can be selected. Specific examples of vectors include, but are not particularly limited to, known vectors described in Japanese Laid-Open Publication No. 11-29599.

Expression vectors can not only synthesize a chimeric protein, but also be used in the agent for restoring visual function or agent for preventing deterioration in visual function of the invention. In other words, the agent for restoring visual function or agent for preventing deterioration in visual function of the invention may comprise, as an active ingredient, an expression vector into which a DNA encoding the amino acid sequence of the aforementioned chimeric protein is incorporated. Such an expression vector can be used in restoring visual function or prevention of deterioration in visual function by direct introduction into a human. As a vector in such use, a vector that can be introduced into a human cell is used. Preferred examples of such a vector include adeno-associated virus vectors (AAV vectors) and lentivirus vectors.

A method of introducing a vector can be appropriately selected depending on the type of host or vector or the like. Specific examples of the method include, but are not particularly limited to, known methods such as the protoplast and competent methods when bacteria are used as the host (see, for example, Japanese Laid-Open Publication No. 11-29599). When an expression vector is used as an active ingredient of the agent for restoring visual function or agent for preventing deterioration in visual function of the invention, the aforementioned AAV vector or the like can be introduced, for example, by injection into the eye.

A host to which an expression vector may be any host that is compatible with the expression vector and can be transformed. Specific examples of the host include, but are not particularly limited to, known naturally-occurring or artificially established cells such as bacteria, yeast, animal cells, and insect cells (see Japanese Laid-Open Publication No. 11-29599) and animals such as humans and mice. A transformant can be cultured by suitably selecting a medium from known nutrient media depending on the type of the transformant or the like and appropriately adjusting the temperature, pH of the nutrient medium, culture time, and the like, so that a chimeric protein can be readily obtained in large quantities (see, for example, Japanese Laid-Open Publication No. 11-29599).

An isolation method and purification method of a chimeric protein is not particularly limited. Examples thereof include known methods such as methods of utilizing solubility, methods utilizing the difference in molecular weights, and methods utilizing charges (see, for example, Japanese Laid-Open Publication No. 11-29599).

As used herein, "active ingredient" refers to an ingredient contained at an amount needed to attain the effect of restoring visual function or the effect of preventing deterioration in visual function. Other ingredients may also be contained, as long as the effect is not reduced below a desired level. The agent for restoring visual function or agent for preventing deterioration in visual function of the invention may also be formulated. Further, the route of administration of the agent for restoring visual function or agent for preventing deterioration in visual function of the invention may be either oral or parenteral. The route of administration can be appropriately determined depending on the form of formulation or the like.

For oral administration, the agent may be formulated into various forms such as tablets, granules, fine granules, powder, and capsules for use. An additive commonly used in a formulation such as a binding agent, covering agent, excipient, lubricant, disintegrant, or humectant may also be included. In addition thereto, formulations for oral administration may be formulated as a liquid formulation such as an aqueous solution for internal use, suspension, emulsion, or syrup. The formulation may also be formulated as a dry formulation that is dissolved in a solvent upon use.

For parenteral administration, the agent may be formulated to be contained in a unit dose ampule or multidose container or tube. An additive such as a stabilizer, buffer, preservative, or isotonizing agent may also be included. A formulation for parenteral administration may also be formulated into a powder form that can be dissolved in a suitable carrier (sterilized water or the like) upon use.

Examples of parenteral administration include intravitreal administration, subconjunctival administration, intra-anterior chamber administration, and eye drops, and intravitreal administration is preferred.

The agent for restoring visual function or agent for preventing deterioration in visual function of the invention discussed above can be used for restoring visual function or preventing deterioration in visual function by administration to humans using the aforementioned method.

As use herein, "visual function restoration" refers to improvement of deteriorated visual function, which may be a partial or complete restoration of the visual function. Further, "prevention of deterioration in visual function" refers to prevention of deterioration in visual function, suppression of progression in deterioration of visual function, and the like. Examples of such visual function include vision, contrast sensitivity, light adaptation, color perception, and the like.

The agent for restoring visual function or agent for preventing deterioration in visual function of the invention may be used in applications expected from restoration of visual function or prevention of deterioration in visual function. For example, the agent may be used in treating or preventing a disease associated with deterioration in visual function. Examples of diseases associated with deterioration in visual function include retinitis pigmentosa, age related macular degeneration, myopic maculopathy, macular dystrophy, diabetic retinopathy, uveitis, retinal detachment, and the like.

<Vector>

The present invention includes adeno-associated virus (AAV) vectors and lentivirus vectors, to which a sequence of a chimeric protein having an amino acid sequence of a microorganism derived ion transport receptor rhodopsin and an amino acid sequence of an animal derived G protein-coupled receptor rhodopsin is inserted.

The present invention also includes the use of an adeno-associated virus (AAV) vector or lentivirus vector, to which a sequence of a chimeric protein having an amino acid sequence of a microorganism derived ion transport receptor rhodopsin and an amino acid sequence of an animal derived G protein-coupled receptor rhodopsin is inserted, for the manufacture of a medicament for restoring visual function or preventing deterioration in visual function.

The same chimeric protein discussed above can be used as the chimeric protein.

EXAMPLES

Experiments related to visual function were conducted using mice as described below.

(Experimental Animal)

For the experiments, wild-type mouse (C57BL/6J, CLEA Japan Inc.) and retinitis pigmentosa model (rdl) mouse (C3H/HeJ Jcls, CLEA Japan Inc.) were used, which were both 3-week old male.

(Production of DNA encoding chimeric protein (GR/BvRh) A DNA encoding a chimeric protein, in which a sequence corresponding to 137th to 145th amino acids from the N-terminus corresponding to the second loop on the cytoplasm side of *Gloeobacter violaceus* Rhodopsin ((GR), SEQ ID NO: 8) was replaced with a sequence corresponding to 137th to 145th amino acids of a bovine rhodopsin (BvRh) (SEQ ID NO: 9), and a sequence corresponding to 198th to 206th amino acids from the N-terminus corresponding to the third loop on the cytoplasm side of *Gloeobacter violaceus* Rhodopsin was replaced with a sequence corresponding to 225th to 252th amino acids of the bovine rhodopsin, and the 132nd amino acid, glutamic acid, of *Gloeobacter violaceus* Rhodopsin was replaced with glutamine, was inserted into a pCDNA3.1 vector. The mutant was produced by the QuicChange method.

(Production of Adeno-Associated Virus (AAV) Vector to which a Sequence of Chimeric Protein is Inserted)

An EGFP or GR/BvRh gene was subcloned to an AAV2 shuttle plasmid to produce AAV2-CAGGS-EGFP-WPRE-pA (vector for expressing EGFP) and AAV2-CAGGS-GR/BvRh-WPRE-pA (vector for expressing a chimeric protein) as virus expressing constructs. Viral vectors were packaged by transfection of three types of plasmids, i.e., vector plasmid, AAV vector plasmid, and adenovirus helper plasmid, into HEK 293 cells. Cesium chloride method was used for the purification of the viral vectors. In the vectors, "ITR" is an abbreviation for "Inverted Terminal Repeat". "CAGGS" is a sequence of a region of a CAG promoter. "WPRE" is an abbreviation for "woodchuck hepatitis virus post-transcriptional regulatory element". "pA" refers to a peptide tag. "EGFP" is an abbreviation for "enhanced green fluorescent protein".

(Vitreous Body Injection)

A mixture of medetomidine hydrochloride (0.75 mg/kg), midazolam (4 mg/kg), butorphanol tartrate (5 mg/kg) was intraperitoneally administered to a wild-type mouse or retinitis pigmentosa model (rdl) mouse. Under systemic anesthesia, a microsyringe equipped with a 32 gauge needle was used to inject the aforementioned AAV vector ("AAV2-CAGGS-EGFP-WPRE-pA" or "AAV2-CAGGS-GR/BvRh-WPRE-pA") at $1\times10^{12}$ vg/ml and 1 μl, respectively, into the vitreous body from near the or a serrata.

(Reporter Observation)

The retina was extracted from a wild-type mouse injected with AAV2-CAGGS-EGFP-WPRE-pA after 7 weeks from injection and immobilized for 1 hour with 4% paraformaldehyde. The whole-mounted retina was observed under a fluorescence microscope. FIG. 1 shows the result thereof. In FIG. 1, GCL means the ganglion cell layer, INL means the inner nuclear layer, and ONL means the outer nuclear layer. Green fluorescence (e.g., arrow in FIG. 1) was observed in the retina as a result of observation. Thus, it was possible to confirm that vector introduction and expression of a gene of interest were normal.

(Multielectrode Array Recording (MEA))

Figure 2:
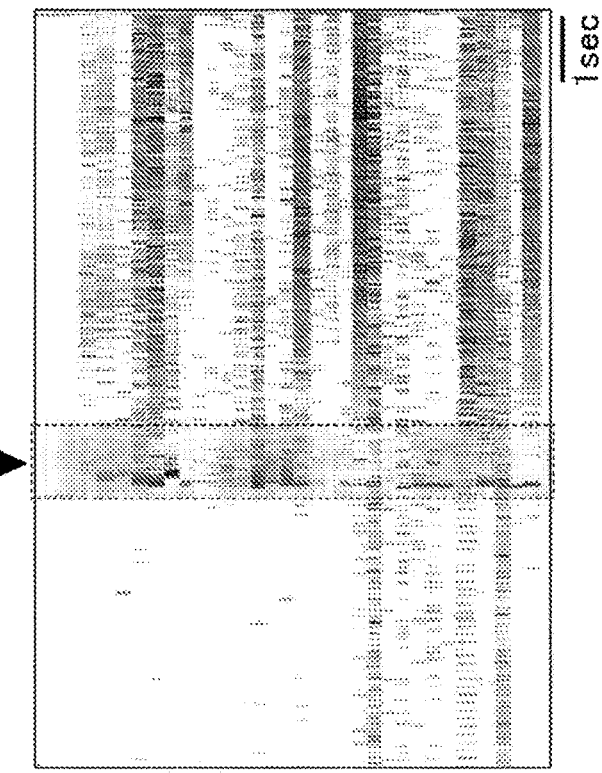
FIG. 2 is (a) a graph of a result of recording extracellular potential of retinal ganglion cells by a multielectrode array (MEA) for a control retinitis pigmentosa model (rdl) mouse, and (b) a graph of a result of recording extracellular potential of retinal ganglion cells by MEA for a retinitis pigmentosa model (rdl) mouse injected with AAV2-CAGGS-GR/BvRh-WPRE-pA.
Figure 2:
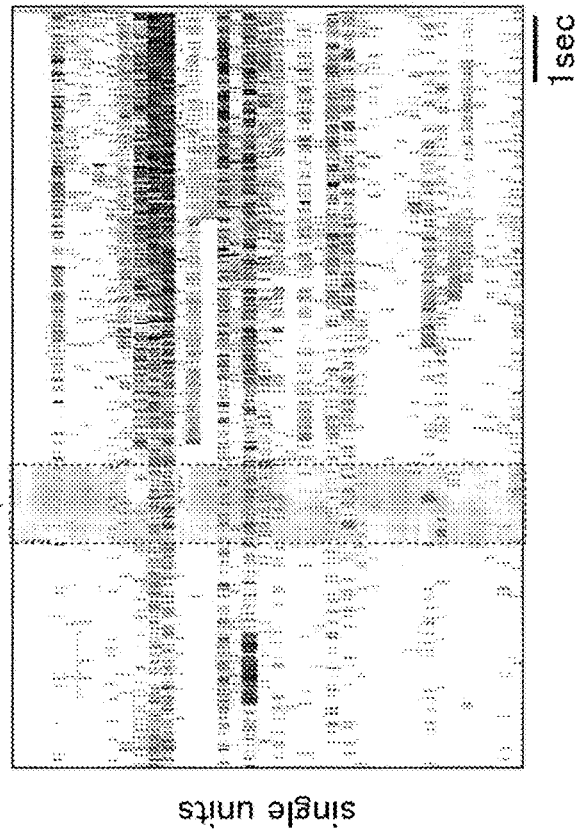

An eye ball was extracted under general anesthesia after 7 weeks from injecting AAV2-CAGGS-GR/BvRh-WPRE-pA to a retinitis pigmentosa model (rdl) mouse. The eye ball was then left standing in an Ames medium (Sigma-Aldrich, St Louis, MO; A1420) bubbled with 95% $O_2$ and 5% $CO_2$, then the retina was extracted. The retina was mounted so that the ganglion cell layer contacted an electrode facing down, and subjected to light stimulation (white light, 1000 cd/m$^2$, 1 second) to record extracellular potential of retinal ganglion cells. Extracellular potential of retinal ganglion cells was also recorded by the same method using a retinitis pigmentosa model (rdl) mouse which had not been injected with AAV2-CAGGS-GR/BvRh-WPRE-pA as a control. A MEA2100-Lite system (Multi-Channel Systems, Reutlingen, Germany) was used for the multielectrode array recording. FIG. 2 shows the results thereof. FIG. 2(*a*) shows a graph for the control mouse, and FIG. 2(*b*) shows a graph for a mouse injected with AAV2-CAGGS-GR/BvRh-WPRE-pA. In the graphs of FIG. 2, the horizontal axis indicates the time elapsed, and the regions indicated by an arrow indicate regions where light stimulation was applied.

As shown in FIG. 2, no change was observed in the region where light stimulation was applied for the control, but it was found that the potential increased for the mouse injected with AAV2-CAGGS-GR/BvRh-WPRE-pA. In view of these results, it was found that GR/BvRh has an effect of restoring visual function against retinitis pigmentosa.

Figure 3:
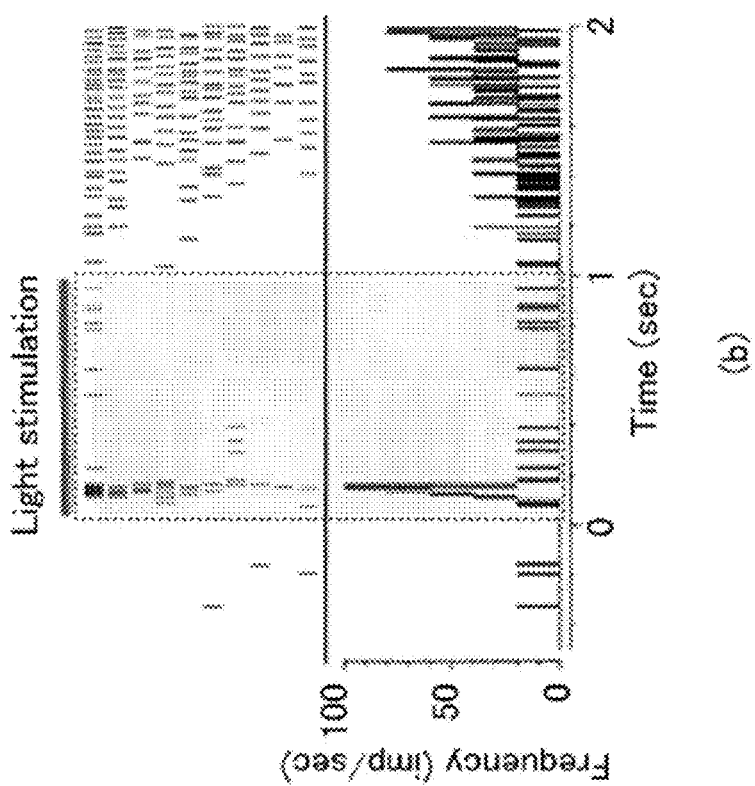
FIG. 3 is a diagram showing a result of recording extracellular potential of retinal ganglion cells by a multielectrode array (MEA) for (a) a control retinitis pigmentosa model (rdl) mouse and (b) a retinitis pigmentosa model (rdl) mouse injected with AAV2-CAGGS-GR/BvRh-WPRE-pA. The top row of FIG. 3 displays a raster plot for 10 firings of retinal ganglion cells, and the bottom row of FIG. 3 is a histogram representing the frequency of firings per second on the vertical axis.
Figure 3:
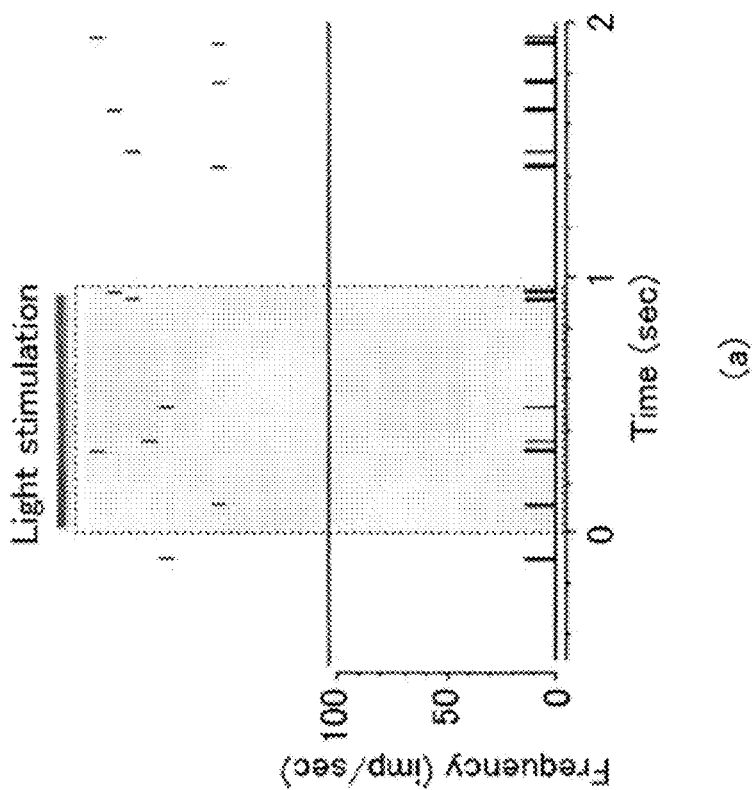

Further, multielectrode array recording was performed by the same approach as above to obtain 10 firings of retinal ganglion cells displayed in a raster plot (top row of FIG. 3), and histograms representing the frequency of firings per second on the vertical axis (bottom row of FIG. 3). Light stimulation was applied from 0 to 1 second. FIG. 3(a) shows a graph for a control mouse, and FIG. 3(b) shows a graph for a mouse injected with AAV2-CAGGS-GR/BvRh-WPRE-pA.

As shown in FIG. 3, a photoresponse was not observed in the control mouse, whereas firing of ganglion cells was observed in the mouse injected with AAV2-CAGGS-GR/BvRh-WPRE-pA, so that a visual restoration effect was observed.

The invention claimed is:

1. A method for treating or preventing a retinal disease in a subject in need therefor or at risk, comprising the step of administering to said subject an effective amount of a nucleic acid molecule comprising a nucleic acid sequence, wherein the nucleic acid sequence encodes a chimeric protein comprising an amino acid sequence of an ion transport receptor rhodopsin derived from a microorganism of the *Gloeobacter* genus and an amino acid sequence of a bovine or human derived G protein-coupled receptor rhodopsin, wherein the chimeric protein comprises an amino acid sequence wherein at least a portion of at least one of a second loop on the cytoplasm side and a third loop on the cytoplasm side of the amino acid sequence of the microorganism derived ion transport receptor rhodopsin is substituted with an amino acid sequence of at least a portion of at least one of a second loop on the cytoplasm side and a third loop on the cytoplasm side of the G protein-coupled receptor rhodopsin, wherein the nucleic acid sequence encodes the amino acid sequence of any one of SEQ ID NOs: 1 to 3.

2. The method of claim 1, wherein the retinal disease is selected from the group consisting of retinitis pigmentosa, age related macular degeneration, myopic maculopathy, macular dystrophy, diabetic retinopathy, and retinal detachment.

3. The method of claim 1, wherein the retinal disease is retinitis pigmentosa.

4. The method according to claim 1, wherein the nucleic acid molecule is incorporated in an expression vector.

5. A method for treating or preventing a retinal disease in a subject in need therefor or at risk, comprising the step of administering to said subject an effective amount of a chimeric protein comprising an amino acid sequence of an ion transport receptor rhodopsin derived from a microorganism of the *Gloeobacter* genus and an amino acid sequence of a bovine or human derived G protein-coupled receptor rhodopsin, wherein the chimeric protein has an amino acid sequence of wherein at least a portion of at least one of a second loop on the cytoplasm side and a third loop on the cytoplasm side of the amino acid sequence of the microorganism derived ion transport receptor rhodopsin is substituted with an amino acid sequence of at least a portion of at least one of a second loop on the cytoplasm side and a third loop on the cytoplasm side of the G protein-coupled receptor rhodopsin, wherein the amino acid sequence is selected from any one of SEQ ID NOs: 1 to 3.

* * * * *

SEQUENCE LISTING

```
<160> NUMBER OF SEQ ID NOS: 9

<210> SEQ ID NO 1
<211> LENGTH: 317
<212> TYPE: PRT
<213> ORGANISM: Artificial Sequence
<220> FEATURE:
<223> OTHER INFORMATION: Artificial Peptide

<400> SEQUENCE: 1

Met Leu Met Thr Val Phe Ser Ser Ala Pro Glu Leu Ala Leu Leu Gly
1               5                   10                  15

Ser Thr Phe Ala Gln Val Asp Pro Ser Asn Leu Ser Val Ser Asp Ser
                20                  25                  30

Leu Thr Tyr Gly Gln Phe Asn Leu Val Tyr Asn Ala Phe Ser Phe Ala
            35                  40                  45

Ile Ala Ala Met Phe Ala Ser Ala Leu Phe Phe Phe Ser Ala Gln Ala
        50                  55                  60

Leu Val Gly Gln Arg Tyr Arg Leu Ala Leu Leu Val Ser Ala Ile Val
65                  70                  75                  80

Val Ser Ile Ala Gly Tyr His Tyr Phe Arg Ile Phe Asn Ser Trp Asp
                85                  90                  95

Ala Ala Tyr Val Leu Glu Asn Gly Val Tyr Ser Leu Thr Ser Glu Lys
                100                 105                 110

Phe Asn Asp Ala Tyr Arg Tyr Val Asp Trp Leu Leu Thr Val Pro Leu
            115                 120                 125

Leu Leu Val Gln Thr Val Ala Val Ile Glu Arg Tyr Val Val Val Cys
130                 135                 140

Lys Pro Met Ser Asn Phe Arg Phe Gly Glu Asn His Pro Leu Leu Ile
145                 150                 155                 160

Lys Leu Thr Val Ala Ser Val Leu Met Ile Ala Thr Gly Tyr Pro Gly
                165                 170                 175

Glu Ile Ser Asp Asp Ile Thr Thr Arg Ile Ile Trp Gly Thr Val Ser
            180                 185                 190

Thr Ile Pro Phe Ala Tyr Ile Leu Tyr Val Leu Trp Val Glu Leu Ser
            195                 200                 205

Phe Thr Val Lys Glu Ala Ala Gln Gln Gln Glu Ser Ala Thr Thr
    210                 215                 220

Gln Val Gln Thr Leu Val Arg Asn Met Arg Trp Leu Leu Leu Leu Ser
225                 230                 235                 240

Trp Gly Val Tyr Pro Ile Ala Tyr Leu Leu Pro Met Leu Gly Val Ser
                245                 250                 255

Gly Thr Ser Ala Ala Val Gly Val Gln Val Gly Tyr Thr Ile Ala Asp
                260                 265                 270
```

Val Leu Ala Lys Pro Val Phe Gly Leu Val Phe Ala Ile Ala Leu
            275                 280                 285

Val Lys Thr Lys Ala Asp Gln Glu Ser Ser Glu Pro His Ala Ala Ile
290                 295                 300

Gly Ala Ala Ala Asn Lys Ser Gly Gly Ser Leu Ile Ser
305                 310                 315

<210> SEQ ID NO 2
<211> LENGTH: 344
<212> TYPE: PRT
<213> ORGANISM: Artificial Sequence
<220> FEATURE:
<223> OTHER INFORMATION: Artificial Peptide

<400> SEQUENCE: 2

Met Leu Met Thr Val Phe Ser Ser Ala Pro Glu Leu Ala Leu Leu Gly
1               5                   10                  15

Ser Thr Phe Ala Gln Val Asp Pro Ser Asn Leu Ser Val Ser Asp Ser
                20                  25                  30

Leu Thr Tyr Gly Gln Phe Asn Leu Val Tyr Asn Ala Phe Ser Phe Ala
            35                  40                  45

Ile Ala Ala Met Phe Ala Ser Ala Leu Phe Phe Phe Ser Ala Gln Ala
        50                  55                  60

Leu Val Gly Gln Arg Tyr Arg Leu Ala Leu Leu Val Ser Ala Ile Val
65                  70                  75                  80

Val Ser Ile Ala Gly Tyr His Tyr Phe Arg Ile Phe Asn Ser Trp Asp
                85                  90                  95

Ala Ala Tyr Val Leu Glu Asn Gly Val Tyr Ser Leu Thr Ser Glu Lys
            100                 105                 110

Phe Asn Asp Ala Tyr Arg Tyr Val Asp Trp Leu Leu Thr Val Pro Leu
        115                 120                 125

Leu Leu Val Gln Thr Val Ala Val Ile Glu Arg Tyr Val Val Val Cys
    130                 135                 140

Lys Pro Met Ser Asn Phe Arg Phe Gly Glu Asn His Pro Leu Leu Ile
145                 150                 155                 160

Lys Leu Thr Val Ala Ser Val Leu Met Ile Ala Thr Gly Tyr Pro Gly
                165                 170                 175

Glu Ile Ser Asp Asp Ile Thr Thr Arg Ile Ile Trp Gly Thr Val Ser
            180                 185                 190

Thr Ile Pro Phe Ala Tyr Ile Leu Tyr Val Leu Trp Val Glu Leu Ser
        195                 200                 205

Phe Thr Val Lys Glu Ala Ala Ala Gln Gln Gln Glu Ser Ala Thr Thr
    210                 215                 220

Gln Val Gln Thr Leu Val Arg Asn Met Arg Trp Leu Leu Leu Leu Ser
225                 230                 235                 240

Trp Gly Val Tyr Pro Ile Ala Tyr Leu Leu Pro Met Leu Gly Val Ser
                245                 250                 255

Gly Thr Ser Ala Ala Val Gly Val Gln Val Gly Tyr Thr Ile Ala Asp
            260                 265                 270

Val Leu Ala Lys Pro Val Phe Gly Leu Val Phe Ala Ile Ala Leu
        275                 280                 285

Val Lys Thr Lys Ala Asp Gln Glu Ser Ser Glu Pro His Ala Ala Ile
    290                 295                 300

Gly Ala Ala Ala Asn Lys Ser Gly Gly Ser Leu Ile Ser Gly Ser Ala
305                 310                 315                 320

-continued

Ser Ala Ser Asn Gly Ala Ser Asp Tyr Lys Asp Asp Asp Lys Glu
                325                 330                 335

Phe Phe Cys Tyr Glu Asn Glu Val
            340

<210> SEQ ID NO 3
<211> LENGTH: 344
<212> TYPE: PRT
<213> ORGANISM: Artificial Sequence
<220> FEATURE:
<223> OTHER INFORMATION: Artificial Peptide

<400> SEQUENCE: 3

Met Leu Met Thr Val Phe Ser Ser Ala Pro Glu Leu Ala Leu Leu Gly
1               5                   10                  15

Ser Thr Phe Ala Gln Val Asp Pro Ser Asn Leu Ser Val Ser Asp Ser
            20                  25                  30

Leu Thr Tyr Gly Gln Phe Asn Leu Val Tyr Asn Ala Phe Ser Phe Ala
        35                  40                  45

Ile Ala Ala Met Phe Ala Ser Ala Leu Phe Phe Ser Ala Gln Ala
    50                  55                  60

Leu Val Gly Gln Arg Tyr Arg Leu Ala Leu Leu Val Ser Ala Ile Val
65                  70                  75                  80

Val Ser Ile Ala Gly Tyr His Tyr Phe Arg Ile Phe Asn Ser Trp Asp
                85                  90                  95

Ala Ala Tyr Val Leu Glu Asn Gly Val Tyr Ser Leu Thr Ser Glu Lys
            100                 105                 110

Phe Asn Asp Ala Tyr Arg Tyr Val Asp Trp Leu Leu Thr Val Pro Leu
        115                 120                 125

Leu Leu Val Glu Thr Val Ala Val Ile Glu Arg Tyr Val Val Val Cys
    130                 135                 140

Lys Pro Met Ser Asn Phe Arg Phe Gly Glu Asn His Pro Leu Leu Ile
145                 150                 155                 160

Lys Leu Thr Val Ala Ser Val Leu Met Ile Ala Thr Gly Tyr Pro Gly
                165                 170                 175

Glu Ile Ser Asp Asp Ile Thr Thr Arg Ile Ile Trp Gly Thr Val Ser
            180                 185                 190

Thr Ile Pro Phe Ala Tyr Ile Leu Tyr Val Leu Trp Val Glu Leu Ser
        195                 200                 205

Phe Thr Val Lys Glu Ala Ala Gln Gln Gln Glu Ser Ala Thr Thr
    210                 215                 220

Gln Val Gln Thr Leu Val Arg Asn Met Arg Trp Leu Leu Leu Leu Ser
225                 230                 235                 240

Trp Gly Val Tyr Pro Ile Ala Tyr Leu Leu Pro Met Leu Gly Val Ser
                245                 250                 255

Gly Thr Ser Ala Ala Val Gly Val Gln Val Gly Tyr Thr Ile Ala Asp
            260                 265                 270

Val Leu Ala Lys Pro Val Phe Gly Leu Leu Val Phe Ala Ile Ala Leu
        275                 280                 285

Val Lys Thr Lys Ala Asp Gln Glu Ser Ser Glu Pro His Ala Ala Ile
    290                 295                 300

Gly Ala Ala Ala Asn Lys Ser Gly Gly Ser Leu Ile Ser Gly Ser Ala
305                 310                 315                 320

Ser Ala Ser Asn Gly Ala Ser Asp Tyr Lys Asp Asp Asp Lys Glu
                325                 330                 335

Phe Phe Cys Tyr Glu Asn Glu Val
            340

<210> SEQ ID NO 4
<211> LENGTH: 311
<212> TYPE: PRT
<213> ORGANISM: Artificial Sequence
<220> FEATURE:
<223> OTHER INFORMATION: Artificial Peptide

<400> SEQUENCE: 4

Met Ala Ser Gln Val Val Tyr Gly Glu Trp Ala Ser Thr His Thr Glu
1               5                   10                  15

Cys Tyr Asn Met Ser Arg Ile Asp Ser Thr Phe Val Ser Leu Leu Gln
            20                  25                  30

Leu Val Trp Ala Val Val Ser Gly Cys Gln Thr Ile Phe Met Ile Ser
        35                  40                  45

Arg Ala Pro Lys Val Pro Trp Glu Ser Val Tyr Leu Pro Phe Val Glu
50                  55                  60

Ser Ile Thr Tyr Ala Leu Ala Ser Thr Gly Asn Gly Thr Leu Gln Met
65                  70                  75                  80

Arg Asp Gly Arg Phe Phe Pro Trp Ser Arg Met Ala Ser Trp Leu Cys
                85                  90                  95

Thr Cys Pro Ile Met Leu Gly Gln Ile Ser Asn Met Ile Glu Arg Tyr
            100                 105                 110

Val Val Val Cys Lys Pro Met Ser Asn Phe Arg Phe Gly Glu Asn His
        115                 120                 125

Ile Pro Leu Asn Pro Ile Ala Gln Ala Ala Ser Ile Ile Arg Val Val
130                 135                 140

Met Gly Ile Thr Ala Thr Ile Ser Pro Ala Glu Tyr Met Lys Trp Leu
145                 150                 155                 160

Phe Phe Phe Phe Gly Ala Thr Cys Leu Val Phe Glu Tyr Ser Val Val
                165                 170                 175

Phe Thr Ile Phe Gln Val Gly Leu Phe Thr Val Lys Glu Ala Ala Ala
            180                 185                 190

Gln Gln Gln Glu Ser Ala Thr Thr Gln Ala Gln Lys Val Val Val Arg
        195                 200                 205

Ile Lys Met Leu Arg Leu Ile Phe Phe Ile Ala Trp Thr Met Phe Pro
210                 215                 220

Ile Val Trp Leu Ile Ser Pro Thr Gly Val Cys Val Ile His Glu Asn
225                 230                 235                 240

Val Ser Ala Ile Leu Tyr Leu Leu Ala Asp Gly Leu Cys Lys Asn Thr
                245                 250                 255

Tyr Gly Val Ile Leu Trp Ser Thr Ala Trp Gly Val Leu Glu Gly Lys
            260                 265                 270

Trp Asp Pro Ala Cys Leu Pro Gly Gln Glu Lys Pro Glu Ala Asp Asp
        275                 280                 285

Pro Phe Gly Leu Asn His Glu Lys Asn Ala Pro Pro Asn Asp Glu Val
290                 295                 300

Asn Ile Arg Met Phe Gly Arg
305                 310

<210> SEQ ID NO 5
<211> LENGTH: 11
<212> TYPE: PRT
<213> ORGANISM: Artificial Sequence

```
<220> FEATURE:
<223> OTHER INFORMATION: Artificial Peptide

<400> SEQUENCE: 5

Ile Glu Arg Tyr Val Val Val Cys Lys Pro Met
1               5                   10

<210> SEQ ID NO 6
<211> LENGTH: 20
<212> TYPE: PRT
<213> ORGANISM: Artificial Sequence
<220> FEATURE:
<223> OTHER INFORMATION: Artificial Peptide

<400> SEQUENCE: 6

Ile Glu Arg Tyr Val Val Val Cys Lys Pro Met Ser Asn Phe Arg Phe
1               5                   10                  15

Gly Glu Asn His
            20

<210> SEQ ID NO 7
<211> LENGTH: 17
<212> TYPE: PRT
<213> ORGANISM: Artificial Sequence
<220> FEATURE:
<223> OTHER INFORMATION: Artificial Peptide

<400> SEQUENCE: 7

Phe Thr Val Lys Glu Ala Ala Gln Gln Gln Glu Ser Ala Thr Thr
1               5                   10                  15

Gln

<210> SEQ ID NO 8
<211> LENGTH: 298
<212> TYPE: PRT
<213> ORGANISM: Gloeobacter violaceus

<400> SEQUENCE: 8

Met Leu Met Thr Val Phe Ser Ser Ala Pro Glu Leu Ala Leu Leu Gly
1               5                   10                  15

Ser Thr Phe Ala Gln Val Asp Pro Ser Asn Leu Ser Val Ser Asp Ser
                20                  25                  30

Leu Thr Tyr Gly Gln Phe Asn Leu Val Tyr Asn Ala Phe Ser Phe Ala
            35                  40                  45

Ile Ala Ala Met Phe Ala Ser Ala Leu Phe Phe Ser Ala Gln Ala
        50                  55                  60

Leu Val Gly Gln Arg Tyr Arg Leu Ala Leu Leu Val Ser Ala Ile Val
65                  70                  75                  80

Val Ser Ile Ala Gly Tyr His Tyr Phe Arg Ile Phe Asn Ser Trp Asp
                85                  90                  95

Ala Ala Tyr Val Leu Glu Asn Gly Val Tyr Ser Leu Thr Ser Glu Lys
            100                 105                 110

Phe Asn Asp Ala Tyr Arg Tyr Val Asp Trp Leu Leu Thr Val Pro Leu
        115                 120                 125

Leu Leu Val Glu Thr Val Ala Val Leu Thr Leu Pro Ala Lys Glu Ala
    130                 135                 140

Arg Pro Leu Leu Ile Lys Leu Thr Val Ala Ser Val Leu Met Ile Ala
145                 150                 155                 160

Thr Gly Tyr Pro Gly Glu Ile Ser Asp Asp Ile Thr Thr Arg Ile Ile
                165                 170                 175
```

```
Trp Gly Thr Val Ser Thr Ile Pro Phe Ala Tyr Ile Leu Tyr Val Leu
            180                 185                 190

Trp Val Glu Leu Ser Arg Ser Leu Val Arg Gln Pro Ala Ala Val Gln
        195                 200                 205

Thr Leu Val Arg Asn Met Arg Trp Leu Leu Leu Ser Trp Gly Val
    210                 215                 220

Tyr Pro Ile Ala Tyr Leu Leu Pro Met Leu Gly Val Ser Gly Thr Ser
225                 230                 235                 240

Ala Ala Val Gly Val Gln Val Gly Tyr Thr Ile Ala Asp Val Leu Ala
                245                 250                 255

Lys Pro Val Phe Gly Leu Leu Val Phe Ala Ile Ala Leu Val Lys Thr
                260                 265                 270

Lys Ala Asp Gln Glu Ser Ser Glu Pro His Ala Ala Ile Gly Ala Ala
                275                 280                 285

Ala Asn Lys Ser Gly Gly Ser Leu Ile Ser
                290                 295

<210> SEQ ID NO 9
<211> LENGTH: 348
<212> TYPE: PRT
<213> ORGANISM: Bos taurus

<400> SEQUENCE: 9

Met Asn Gly Thr Glu Gly Pro Asn Phe Tyr Val Pro Phe Ser Asn Lys
1               5                   10                  15

Thr Gly Val Val Arg Ser Pro Phe Glu Ala Pro Gln Tyr Tyr Leu Ala
            20                  25                  30

Glu Pro Trp Gln Phe Ser Met Leu Ala Ala Tyr Met Phe Leu Leu Ile
        35                  40                  45

Met Leu Gly Phe Pro Ile Asn Phe Leu Thr Leu Tyr Val Thr Val Gln
    50                  55                  60

His Lys Lys Leu Arg Thr Pro Leu Asn Tyr Ile Leu Leu Asn Leu Ala
65                  70                  75                  80

Val Ala Asp Leu Phe Met Val Phe Gly Gly Phe Thr Thr Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
        115                 120                 125

Val Val Leu Ala Ile Glu Arg Tyr Val Val Val Cys Lys Pro Met Ser
    130                 135                 140

Asn Phe Arg Phe Gly Glu Asn His Ala Ile Met Gly Val Ala Phe Thr
145                 150                 155                 160

Trp Val Met Ala Leu Ala Cys Ala Ala Pro Pro Leu Val Gly Trp Ser
                165                 170                 175

Arg Tyr Ile Pro Glu Gly Met Gln Cys Ser Cys Gly Ile Asp Tyr Tyr
            180                 185                 190

Thr Pro His Glu Glu Thr Asn Asn Glu Ser Phe Val Ile Tyr Met Phe
        195                 200                 205

Val Val His Phe Ile Ile Pro Leu Ile Val Ile Phe Phe Cys Tyr Gly
    210                 215                 220

Gln Leu Val Phe Thr Val Lys Glu Ala Ala Ala Gln Gln Gln Glu Ser
225                 230                 235                 240
```

```
Ala Thr Thr Gln Lys Ala Glu Lys Glu Val Thr Arg Met Val Ile Ile
            245             250                 255

Met Val Ile Ala Phe Leu Ile Cys Trp Leu Pro Tyr Ala Gly Val Ala
            260             265                 270

Phe Tyr Ile Phe Thr His Gln Gly Ser Asp Phe Gly Pro Ile Phe Met
        275             280                 285

Thr Ile Pro Ala Phe Phe Ala Lys Thr Ser Ala Val Tyr Asn Pro Val
        290             295             300

Ile Tyr Ile Met Met Asn Lys Gln Phe Arg Asn Cys Met Val Thr Thr
305             310             315                         320

Leu Cys Cys Gly Lys Asn Pro Leu Gly Asp Asp Glu Ala Ser Thr Thr
            325             330                 335

Val Ser Lys Thr Glu Thr Ser Gln Val Ala Pro Ala
            340             345
```